United States Patent [19]
Valkirs

[11] Patent Number: 5,851,776
[45] Date of Patent: *Dec. 22, 1998

[54] CONJUGATES AND ASSAYS FOR SIMULTANEOUS DETECTION OF MULTIPLE LIGANDS

[75] Inventor: Gunars E. Valkirs, Escondido, Calif.

[73] Assignee: Biosite Diagnostics, Inc., San Diego, Calif.

[*] Notice: The portion of the term of this patent subsequent to Jul. 2, 2008, has been disclaimed.

[21] Appl. No.: 101,782

[22] Filed: Aug. 3, 1993

Related U.S. Application Data

[63] Continuation of Ser. No. 685,084, Apr. 11, 1991, abandoned.
[51] Int. Cl.$^6$ .................................................. G01N 33/53
[52] U.S. Cl. ................................................................ 435/7.1
[58] Field of Search .............................. 435/7.1, 7.4, 7.5, 435/7.6, 7.7, 7.71, 7.72, 7.8, 7.9, 7.91, 7.92, 7.93, 7.94, 7.95

[56] References Cited

U.S. PATENT DOCUMENTS

| | | | |
|---|---|---|---|
| 4,444,878 | 4/1984 | Paulus | 435/7.1 |
| 4,868,109 | 9/1989 | Lansdorp | 435/28 |
| 5,028,535 | 7/1991 | Buechler et al. | 435/7.1 |

OTHER PUBLICATIONS

Brennan et al (1985) Science 229, 81–83.

*Primary Examiner*—James Ketter
*Attorney, Agent, or Firm*—Lyon & Lyon LLP

[57] ABSTRACT

Novel conjugates and competitive and non-competitive assays for simultaneously detecting the presence or amount of at least two target ligands capable of competing with a single conjugate for binding to at least two different ligand receptors. The invention teaches and claims binding domains coupled to a signal development element to form a conjugate where each binding domain comprises at least one ligand analogue or ligand receptor depending on assay design. The binding domains are constructed such that they function independently from one another in assays for their respective target ligands. Each binding domain may bind its respective binding partners in the assay without affecting the binding reactions of other binding domains coupled to the same signal development element.

25 Claims, No Drawings

100
CONJUGATES AND ASSAYS FOR SIMULTANEOUS DETECTION OF MULTIPLE LIGANDS

This application is a continuation of application Ser. No. 07/685,084, filed Apr. 11, 1991, now abandoned.

FIELD OF THE INVENTION

This invention is in the field of ligand-receptor assays for the simultaneous detection of multiple selected target ligands in a fluid sample.

BACKGROUND OF THE INVENTION

As used herein, the term "ligand-receptor assay" refers to an assay for at least one target ligand which may be detected by the formation of a complex between the ligand and a receptor capable of binding with that target ligand. The target ligand may be the analyte itself or a substance which, if detected, can be used to infer the presence of the analyte in a sample. In the context of the present invention, the term "ligand", includes haptens, hormones, peptides, proteins, deoxyribonucleic acid (DNA), ribonucleic acids (RNA), metabolites of the aforementioned materials and other substances of either natural or synthetic origin which may be of diagnostic interest and have a specific ligand receptor therefor. Ligand-receptor assays are generally useful for the in vitro determination of the presence and concentration of ligands in body fluids, food products, animal fluids, and environmental samples. For example, the determination of specific hormones, peptides, proteins, therapeutic drugs, and toxic drugs in human blood or urine has significantly improved the medical diagnosis of the human condition. There is a continuing need for simple, rapid assays for the qualitative, semi-quantitative, and quantitative determination of such ligands in a sample. Furthermore, in many situations, such assays need to be simple enough to be performed and interpreted by non-technical users.

Ligand-receptor assays rely on the binding of target ligands by ligand receptors to determine the concentrations of target ligands in a sample. Ligand-receptor assays can be described as either competitive or non-competitive. Competitive assays generally involve a sample suspected of containing target ligand, a ligand analogue conjugate, and the competition of these species for a limited number of binding sites provided by the ligand receptor. Those skilled in the art will appreciate that many variations of this basic competitive situation have been previously described and will not be discussed in detail herein except where pertinent to the general objectives of this invention.

Competitive ligand-receptor assays can be further described as being either homogeneous or heterogeneous. In homogeneous assays all of the reactants participating in the competition are mixed together and the quantity of target ligand is determined by its effect on the extent of binding between ligand receptor and ligand analogue conjugate. The signal observed is modulated by the extent of this binding and can be related to the amount of target ligand in the sample. U.S. Pat. No. 3,817,837 describes such a homogeneous, competitive ligand-receptor assay.

Heterogeneous, competitive ligand-receptor assays require a separation of ligand analogue conjugate bound to ligand receptor from the free ligand analogue conjugate and measurements of either the bound or the free fractions. Methods for performing such assays are described in U.S. Pat. Nos. 3,654,090, 4,298,685, 4,425,438, and 4,506,009, European Patent Application 87309724.0, and PCT International Application No. PCT/US86/00668. Separation of the bound from the free may be accomplished by removal of the ligand receptor and anything bound to it from the free ligand analogue conjugate by immobilization of the ligand receptor on a solid phase or precipitation. The amount of the ligand analogue conjugate in the bound or the free fraction can then be determined and related to the concentration of the target ligand in the sample. Normally the bound fraction is in a convenient form, for example, on a solid phase, so that it can be washed, if necessary, to remove remaining unbound ligand analogue conjugate and the measurement of the bound ligand analogue conjugate or related products is facilitated. The free fraction is normally in a liquid form that is generally inconvenient for measurements. If multiple ligands are being determined in a single assay, the determination of the free fraction of ligand analogue conjugate for each ligand is made impossible if all are mixed in a single liquid unless the responses of the individual ligand analogue conjugates can be distinguished in some manner. However, detecting the free fraction of ligand analogue conjugate in assays that are visually interpreted is a distinct advantage because the density of the color developed in such assays is generally proportional to the ligand concentration over much of the range of ligand concentration.

One method that can be used to detect the free ligand analogue conjugate in a heterogeneous, competitive ligand-receptor assay process is to provide a second, immobilized receptor specific for the target ligand on a solid phase so that the ligand analogue conjugate not bound to the first ligand receptor can be bound to the second ligand receptor immobilized on the solid phase. Methods for performing such assays are described in U.S. patent application Ser. No. 295,568, filed on Jan. 10, 1989, and in European Patent Application 90300283.0, both of which are hereby incorporated by reference. In order to assay for the presence or amount of multiple ligands in a sample by such methods, one skilled in the art would utilize either multiple, separate assays, each assay directed toward one of the ligands of interest, or a single assay with a mixture of ligand analogue conjugates, each conjugate specific for one of the target ligands. Multiple, separate assays, such as screens for drugs of abuse, are consumptive of time, labor, and materials. An alternative assay that is more efficient utilizes a mixture of ligand analogue conjugates, ligand receptors, and the sample to generate simultaneous competitive binding reactions for multiple target ligands. The presence or amount of each target ligand is subsequently determined by contacting the reaction mixture with receptors on a solid phase that are immobilized in discrete zones specific for the individual ligand analogue conjugates in the reaction mixture, developing the signals from the bound ligand analogue conjugates, and relating the detectable signals to those produced by standards. Assays utilizing mixtures of ligand analogue conjugates suffer from increased non-specific signal development that is generally proportional to the concentration of the signal development element used in the assay. If ten ligand analogue conjugates are mixed at concentrations that would be needed in separate assays, the resulting mixture would exhibit non-specific signal development that is approximately ten times the amount observed in assays utilizing single ligand analogue conjugates. The sensitivity of ligand receptor assays is usually limited in practice by the signal developed due to non-specific binding. Assays utilizing mixtures of ligand analogue conjugates would therefore result in decreased sensitivity for each target ligand. A reduction in the concentration of the signal development element used in each ligand analogue conjugate to reduce the non-specific signal would decrease the maximum assay responses and result in poorer assay sensitivities and smaller ranges of concentrations for the assays. The benefits of efficiency gained by using mixtures of the ligand analogue conjugates in order to simultaneously assay multiple target ligands in a sample are offset by the losses in sensitivity and assay range that result. The present invention overcomes these deficiencies.

The method described in U.S. Pat. No. 4,506,009 utilizes a ligand analogue conjugate which has both the ligand analogue and an insolubilizing binding component which is a different ligand coupled to the signal development element. An insolubilizing receptor is used to precipitate the free ligand analogue conjugate unless it is sterically hindered by the binding of the antibody specific for target ligand to the ligand analogue. This invention makes use of the physical relationship between the two ligands coupled to the same signal development element and it shows that two ligands cannot generally be bound to the same signal development element such that the ligand-receptor binding reactions remain independent. If such conjugates are used in assays for two target ligands, the binding of ligand receptor to the first target ligand will affect the binding of the other ligand receptor to the second target ligand. The two target ligands cannot be accurately assayed using such conjugates. The prior art offers no solution to enable the simultaneous assay of multiple target ligands in a sample except the use of mixtures of ligand analogue conjugates which suffers from the deficiencies previously described.

Non-competitive assays generally utilize ligand receptors in substantial excess over the concentration of target ligand to be determined in the assay. Sandwich assays, in which the target ligand is detected by binding to two ligand receptors, one ligand receptor present in the form of a ligand receptor conjugate and a second ligand receptor, frequently bound to a solid phase, to facilitate separation from unbound reagents, such as unbound first ligand receptor conjugate, are examples of non-competitive assays. Assays that utilize ligand receptor conjugates include both competitive and non-competitive assays. If multiple target ligands are assayed in a single sample using mixtures of ligand receptor conjugates, the problems of increased non-specific binding and decreased sensitivity arise for the same reasons described for mixtures of ligand analogue conjugates. The present invention facilitates the simultaneous assay of multiple ligands in a sample by utilizing ligand analogues or ligand receptors in binding domains coupled to a single signal development element to form a conjugate. Such conjugates can permit the simultaneous assay of multiple ligands in a sample without losses in sensitivity or assay range that are associated with the use of mixtures of individual ligand receptor conjugates.

This invention overcomes deficiencies of the prior art methods. It describes assay processes utilizing conjugates wherein a signal development element is coupled to at least two binding domains, each binding domain having ligand analogues or ligand receptors, for the assay of at least two target ligands in a sample.

SUMMARY OF THE INVENTION

The present invention teaches and claims binding domains coupled to a signal development element to form a conjugate where each binding domain comprises at least one ligand analogue or ligand receptor depending on assay design. The binding domains are constructed such that they function independently from one another in assays for their respective target ligands. Each binding domain may bind its respective binding partners in the assay without affecting the binding reactions of other binding domains coupled to the same signal development element. The novel conjugates of the present invention are useful in heterogeneous assay processes for the detection of multiple target ligands in a sample where the method of detection utilizes a solid phase that has discrete zones specific for the target ligands.

DEFINITIONS

In interpreting the claims and specification, the following terms shall have the meanings set forth below.

Ligand—Binding partner to ligand receptor. A ligand may be a ligand receptor depending on assay design.

Ligand Analogue—A chemical derivative of the target ligand which may be attached either covalently or non-covalently to other species, for example, to the signal development element. Ligand analogue and target ligand may be the same and both are capable of binding to ligand receptor.

Ligand Receptor—Receptor capable of binding ligand, typically an antibody, but which may be a ligand depending on assay design.

Ligand Analogue Conjugate—A conjugate of a ligand analogue and a signal development element. Ligand analogues may be coupled directly to signal development elements or they may be coupled to a protein or polymer and the product may be coupled to a signal development element. Ligand analogue conjugates and their intended ligand receptors are complementary. Ligand analogue conjugates and ligand receptors other than their intended ligand receptors are uncomplementary.

Ligand Receptor Conjugate—A conjugate of a ligand receptor and a signal development element. Ligand receptors may be coupled directly to a signal development element or they may be coupled to a protein or polymer and the product may be coupled to a signal development element. Ligand receptor conjugates and their intended ligand or ligand analogues are complementary. Ligand receptor conjugates and ligands or ligand analogues other than the intended targets are uncomplementary.

Conjugate—A signal development element coupled to at least two different binding domains, each binding domain comprising at least one ligand analogue or ligand receptor capable of binding its complementary binding partner.

Signal Development Element—The element a conjugate which, in conjunction with the signal development phase, develops the detectable signal, e.g., an enzyme.

Signal Development Phase—The phase containing the materials enabling the signal development element to develop signal, e.g., an enzyme substrate solution.

Reaction Mixture—In a competitive immunoassay, the mixture of sample suspected of containing the target ligand and the assay reagents that participate in the competitive binding reactions.

Solid Phase—The solid phase upon which is immobilized discrete zones for the detection of target ligands where the signal is finally developed during the signal development step for interpretation of the assay results.

Ligand Analogue Construct—At least one ligand analogue immobilized on a solid phase or coupled to a molecule that is not a signal development element.

DETAILED DESCRIPTION OF THE INVENTION

Heterogeneous, competitive ligand-receptor assays for multiple target ligands in a sample that are described in the prior art utilize a mixture of ligand analogue conjugates, ligand receptors, and a sample suspected of containing the target ligands. The sample may be contacted with the ligand receptors and the ligand analogue conjugates may be added separately or the sample and reagents may be contacted simultaneously to form a reaction mixture. The ligand receptors may be immobilized in discrete zones on a solid phase in order to facilitate the separation of conjugates bound to ligand receptors from the free conjugates. The competitive binding reactions are allowed to proceed to a point where the amounts of the individual ligand analogue conjugates that are bound to their complementary ligand receptors are related to the amounts of the corresponding target ligands in the sample.

The ligand analogue conjugates of the prior art comprised ligand analogues of the target ligand coupled to a signal development element. Ligand analogues for two or more target ligands were not generally coupled to the same signal development element for the assay of multiple target ligands in a sample because the binding of a ligand receptor to a ligand analogue for one target ligand would potentially interfere with the binding of a nearby ligand analogue for another target ligand with its ligand receptor. The higher the density of different ligand analogues on a signal development element, the more likely it becomes that different ligand analogues will be close to one another so that the binding of a ligand receptor to one ligand analogue inhibits the binding of a different ligand receptor to its respective ligand analogue. Under these circumstances, the competitive binding reactions necessary for the assay of one target ligand affect the assay of another target ligand yielding inaccurate assay results. Evidence for such interactions is found in U.S. Pat. No. 4,506,009 which makes use of these interferences in an assay for a single target ligand as described in the background of the present invention. Ligand analogues for different target ligands that are randomly coupled to signal development elements will potentially be subject to such interferences. Lowering the density of ligand analogues for different target ligands that are coupled to a signal development element to densities that insure these effects do not affect assay performance can severely limit the ability of the assay designer to vary the ligand analogue density in order to achieve assay design goals. To avoid these problems, prior art assays use a mixture of ligand analogue conjugates where each signal development element is coupled to ligand analogues for one target ligand to simultaneously assay for multiple target ligands in a sample. The high concentrations of signal development elements required by such mixtures of ligand analogue conjugates can result in high non-specific binding that reduces assay sensitivity for all target ligands in the assay.

Similarly, prior art assays for multiple target ligands in a sample that utilize ligand receptor conjugates in either heterogeneous, competitive assays or heterogeneous, non-competitive assays are performed using mixtures of ligand receptor conjugates. The increased non-specific binding and the resulting loss of sensitivity for each target ligand in such assays are remedied by the present invention.

The conjugates of the present invention have binding domains coupled to a signal development element wherein each binding domain comprises at least one ligand analogue or ligand receptor. The binding domains function independently from one another in assays for their respective target ligands even when the density of binding domains on the signal development element is high. The construction and use of such conjugates is dependent on the assay design.

In heterogeneous, competitive assays that utilize ligand analogues coupled to a signal development, each binding domain comprises at least one ligand analogue coupled to a signal development element such that the binding domain can bind its complementary ligand receptor. If the ligand analogue is, for example, a protein antigen that is similar in size or larger than its complementary ligand receptor, then the ligand analogue can be coupled directly by covalent or non-covalent means to the signal development element to generate a binding domain on the signal development element that can bind to its complementary ligand receptor without interference from uncomplementary ligand receptors that can bind to other binding domains on the signal development element. Those skilled in the art will appreciate that the means used to couple the ligand analogue to the signal development element will not always result in a functional binding domain that can bind to its complementary ligand receptor. Multiple binding domains containing the same ligand analogue can be coupled to a single signal development element to vary the ability of the conjugate to compete with the target ligand for the complementary ligand receptor. If the ligand analogue is substantially smaller than the complementary ligand receptor, then the ligand analogue is first coupled to a molecular structure such as a protein or a polymer that is similar in size or larger than the complementary ligand receptor, preferably by covalent means, and then the product is coupled to the signal development element to generate a binding domain on the signal development element. A functional binding domain must contain at least one ligand analogue capable of binding to its complementary ligand receptor. Those skilled in the art will appreciate that the number of ligand analogues coupled to the molecular structure can be used to vary the ability of the conjugate to compete with the target ligand for the complementary ligand receptor. A particularly preferred embodiment of the present invention is the construction of a conjugate for the assay of multiple target ligands that are haptens in a sample by first coupling ligand analogues for the different target ligands separately to bovine serum albumin (BSA) so that a BSA molecule is coupled only to ligand analogues for a single target ligand. The products are mixed and coupled to a signal development element to generate a mixture of binding domains on a single signal development element. Each BSA molecule coupled to a signal development element and to a number of ligand analogues such that at least one of the ligand analogues is capable of binding to its complementary ligand receptor is a binding domain on the signal development element. Preferred signal development elements include polymers containing dyes, latex particles containing dyes, liposomes containing dyes, and metal sols. A particularly preferred signal development element is colloidal gold. The coupling of a mixture of BSA molecules to colloidal gold, some of the BSA molecules being coupled to one type of ligand analogue, can be achieved by adsorption. Methods for coupling ligand analogues to proteins and for adsorption of proteins to colloidal gold are well known to those skilled in the art, see, for example, U.S. Pat. Nos. 3,817,837, 3,878,187, 3,884,898, 4,203,802, 4,281,065, 4,313,734, Rodgers, et al., *Clinical Chemistry*, 24, 95–100 (1976) and Georghegan, et al., *J. Histochem. Cytochem.*, 25, 1187–1200 (1977). The labeling ratios of ligand analogue to BSA and the relative proportions of BSA molecules coupled to ligand analogues that are mixed with unlabeled BSA or with other proteins for adsorption to colloidal gold are empirically determined by assay performance. When used in heterogeneous, competitive assays with antibodies specific for the target ligands, such conjugates have been successfully used in an assay for multiple target ligands in a sample. The linkage chemistries used to couple different ligand analogues to signal development elements have similarities that result in low affinity binding interactions between ligand analogues in binding domains and uncomplementary ligand receptors that are either in solution or are immobilized on the solid phase. Such undesirable binding interactions are substantially eliminated by the incorporation of crosstalk inhibitors in the reaction mixture such as those described in co-pending application titled Crosstalk Inhibitors and Their Use in Assays, filed on even date herewith which is hereby incorporated by reference.

In heterogeneous assays of the present invention that utilize ligand receptors coupled to a signal development element, each binding domain comprises at least one ligand receptor coupled to a signal development element such that the binding domain is capable of binding to its target ligand in non-competitive assays or to target ligand, ligand analogues, or ligand analogue constructs in competitive assays. In order for a ligand receptor that is coupled to a signal development element to function as a binding domain, it must be able to bind to its target ligand, ligand analogue, or ligand analogue construct without being affected by the binding events occurring at nearby uncomplementary binding domains on the same signal development element. The ligand receptor should be of similar size or larger than the target ligand, ligand analogue, or ligand analogue construct. If this is not the case, ligand receptors for the same target ligand can be coupled to one another to generate aggregates of ligand receptor that can then be coupled to a signal development element to generate a binding domain. In the present invention preferred ligand receptors are antibodies. Preferred signal development elements include polymers containing dyes, latex particles containing dyes, liposomes containing dyes, and metal sols. A particularly preferred signal development element is colloidal gold. Particularly preferred are conjugates formed by mixing different monoclonal antibodies together prior to adsorption onto colloidal gold. The optimum mixtures of ligand receptors and other proteins or polymers that are coupled to a signal development element are dependent on the particular objectives of an assay and are empirically determined.

In some heterogeneous, competitive assay processes of the present invention, the reaction mixture is formed by contacting the sample, a conjugate comprising at least two different binding domains coupled to a signal development element, each different binding domain capable of binding ligand receptors for a target ligand, and ligand receptors that are immobilized in discrete zones on a solid phase, each zone being specific for a target ligand. The reaction mixture is allowed to incubate until the amounts of conjugate bound to the ligand receptor zones are related to the concentrations of the target ligands in the sample. Alternatively, the sample is contacted with the solid phase followed by contact of the conjugate with the solid phase. The unbound conjugate may be washed away from the solid phase before contact with a signal development phase or methods such as those described in U.S. Pat. Nos. 4,233,402 and 4,391,904 may be employed to develop the signal without washing. The signal developed at each discrete zone of immobilized ligand receptor is related to the concentration of its respective target ligand by calibration methods well-known to those skilled in the art. It is important to note that the discrete zones of immobilized ligand receptors must be separated in space by a sufficient distance so that binding of conjugate to one zone does not deplete the concentration of conjugate available for competitive reactions in a neighboring zone. Solid phases where the ligand receptor zones are immobilized on a surface such as a porous membrane are preferred for this reason.

In other heterogeneous, competitive assay processes of the present invention the reaction mixture is formed by contacting the sample, soluble ligand receptors for each target ligand, and a conjugate comprising at least two different binding domains coupled to a signal development element, each different binding domain capable of binding ligand receptors for a target ligand. The reaction mixture is allowed to incubate until the amounts of binding domains not bound to the ligand receptors are related to the amounts of the target ligands in the sample. The reaction mixture is then contacted with a solid phase comprising discrete zones of immobilized ligand receptors, each zone being specific for a target ligand. The binding domains on the conjugate that are not bound by ligand receptors are able to bind to their respective zones on the solid phase. The unbound conjugate may be washed away from the solid phase before contact with a signal development phase or methods such as those described in U.S. Pat. Nos. 4,233,402 and 4,391,904 may be employed to develop the signal without washing. The signal developed at each discrete zone of immobilized ligand receptor is related to the concentration of its respective target ligand by calibration methods well-known to those skilled in the art. The conjugates of the present invention, when used instead of mixtures of ligand analogue conjugates in assay methods and devices such as those described in U.S. Pat. Nos. 4,632,901, 4,727,019, 4,959,307, 4,963,468, and European Patent Application 90300283.0 substantially improve the simultaneous assay of multiple target ligands in a sample. Preferred assay methods employ a solid phase which contains receptors immobilized in discrete zones on a porous member, each zone being specific for one of the target ligands. Particularly preferred assay methods employ solid phases with discrete zones containing immobilized ligand analogue antibodies such as those described in co-pending U.S. patent application Ser. No. 583,046, filed on Sep. 14, 1990.

In some heterogeneous, competitive assay processes of the present invention, the reaction mixture is formed by contacting the sample, a conjugate comprising at least two different binding domains coupled to a signal development element, each different binding domain comprising at least one ligand receptor capable of binding its target ligand, and ligand analogues that are immobilized in discrete zones on a solid phase, each zone being specific for a target ligand. The reaction mixture is allowed to incubate until the amounts of conjugate bound to the ligand analogue zones are related to the concentrations of the target ligands in the sample. Alternatively, the sample is contacted with the solid phase followed by contact of the conjugate with the solid phase. The unbound conjugate may be washed away from the solid phase before contact with a signal development phase or methods such as those described in U.S. Pat. Nos. 4,233,402 and 4,391,904 may be employed to develop the signal without washing. The signal developed at each discrete zone of immobilized ligand analogues is related to the concentration of its respective target ligand by calibration methods well-known to those skilled in the art. It is important to note that the discrete zones of immobilized ligand analogues must be separated in space by a sufficient distance so that binding of conjugate to one zone does not deplete the concentration of conjugate available for competitive reactions in a neighboring zone. Solid phases where the ligand analogue zones are immobilized on a surface such as a porous membrane are preferred for this reason.

In other heterogeneous, competitive assay processes of the present invention the reaction mixture is formed by contacting the sample, ligand analogue constructs for each target ligand, and a conjugate comprising at least two different binding domains coupled to a signal development element, each different binding domain comprising at least one ligand receptor capable of binding its target ligand. The reaction mixture is allowed to incubate until the amounts of binding domains not bound to the ligand analogue constructs are related to the amounts of the target ligands in the sample. The reaction mixture is then contacted with a solid phase comprising discrete zones of immobilized ligand analogues, each zone being specific for a target ligand. The binding domains on the conjugate that are not bound by ligand analogue constructs are able to bind to their respective zones on the solid phase. The unbound conjugate may be washed away from the solid phase before contact with a signal development phase or methods such as those described in U.S. Pat. Nos. 4,233,402 and 4,391,904 may be employed to develop the signal without washing. The signal developed at each discrete zone of immobilized ligand analogues is related to the concentration of its respective target ligand by calibration methods well-known to those skilled in the art. The conjugates of the present invention, when used instead of mixtures of ligand receptor conjugates in assay methods and devices such as those described in U.S. Pat. Nos. 4,632,901, 4,727,019, 4,959,307, 4,963,468, and European Patent Application 90300283.0 substantially improve the simultaneous assay of multiple target ligands in a sample. Preferred assay methods employ a solid phase which contains ligand analogues immobilized in discrete zones on a porous member, each zone being specific for one of the target ligands.

In heterogeneous, non-competitive assay processes of the present invention, the sample is contacted with a solid phase which contains ligand receptors immobilized in discrete zones specific for each target ligand. The solid phase can then be contacted with the conjugate of the present invention. The conjugate comprises at least two different binding domains coupled to a signal development element, each different binding domain comprising at least one ligand receptor capable of binding its target ligand. Alternatively, the sample can be contacted with the conjugate and then with the solid phase. Preferred methods and devices for the practice of heterogeneous, non-competitive assays processes are described in U.S. Pat. No. 4,727,019. The conjugates of the present invention, when used instead of mixtures of ligand receptor conjugates in such assay processes, substantially improve the ability to simultaneously assay multiple target ligands in a sample.

In heterogeneous assays it is often advantageous to include internal calibration or control functions in the assay to provide information in addition to the response generated due to the interaction of the target ligand with the assay reagents. One such function is to provide internal references that enable the qualitative or quantitative determination of the target ligand concentration without calibration by additional assays. Such methods are described in U.S. Pat. No. 4,849,338 and European Patent Applications 87302403.8 and 90300283.0. These methods can be practiced by coupling ligands other than the ligand analogues of the target ligand to signal development elements. The coupling of such ligands to molecular structures and then to a signal development element can generate binding domains for these ligands. Conjugates that are comprised of two different binding domains where one binding domain is used to assay for the target ligand and the other binding domain is used, for example, as a means for internal calibration of the assay are substantial improvements over the prior art because the binding reactions at the two binding domains can be independently optimized without affecting one another. Conjugates that have binding domains for the assay of a target ligand and binding domains for internal reference or control functions are considered to be part of the present invention even if the assay is designed for a single target ligand.

The present invention describes conjugates that are used in the assay of multiple target ligands in a sample. While it is possible to construct single conjugates which contain all the binding domains necessary for the assay of all the target ligands in a sample, practical considerations will generally favor the construction of conjugates that are used in the assay of certain combinations or panels of target ligands. Such conjugates can be further combined in an assay for any combination of such panels of target ligands in a sample.

Assays for multiple target ligands can also be performed using a conjugate comprising a combination of binding domains on a signal development element, some binding domains comprising ligand analogues and some binding domains comprising ligand receptors. In such assays, one target ligand can be detected by a heterogeneous, competitive assay process and another target ligand can be detected by a heterogeneous, non-competitive assay process. Combinations of the different binding domains described herein on a signal development element and heterogeneous assay processes that are combinations of the processes described herein are within the scope of the present invention.

EXAMPLE 1

Reagents and Simultaneous Assay for Amphetamine and Morphine in a Sample

Synthesis of Acetylthiopropionic Acid

To a stirred solution of 3-mercaptopropionic acid (7 ml, 0.08 moles) and imidazole (5.4 g, 0.08 moles) in tetrahydrofuran (THF, 700 ml) was added dropwise over 15 minutes, under argon, a solution of 1-acetyl imidazole (9.6 g, 0.087 moles) in THF (100 ml). The solution was allowed to stir a further 3 hours at room temperature after which time the THF was removed in vacuo. The residue was treated with ice-cold water (18 ml) and the resulting solution acidified with ice-cold concentrated HCl (14.5 ml) to pH 1.5–2. The mixture was extracted with water (2×50 ml), dried over magnesium sulfate and evaporated. The residual crude yellow oily solid product (10.5 g) was recrystallized from chloroform-hexane to afford 4.8 g (41% yield) acetylthiopropionic acid as a white solid with a melting point of 44°–45° C.

Synthesis of 3-O-Carboxymethylmorphine Hydrochloride

Morphine sulfate (1.67 g, $5\times10^{-3}$ mol) was dissolved with potassium carbonate (2.07 g, $1.5\times10^{-2}$ mol) in 80 ml ethanol. The solution was heated to reflux while stirring and a solution containing bromoacetic acid (0.7 g, $5\times10^{-3}$ mol) was added in 2 ml ethanol. This was refluxed for 2 hr, then the flask was cooled in an ice-water bath. The pH was adjusted to 3 with 12N hydrochloric acid and precipitates were filtered. Solvents were evaporated in vacuo and 10 ml ethanol was added to the residue. Precipitates were filtered and solvents evaporated in vacuo. The residue was recrystallized from water/acetone (10:90). Approximately 300 mg of product was recovered.

Synthesis of 3-0-[2-(2-Amino-4-Thiolbutanoic Acid Thiolactone)-Acetamide]-Morphine Hydrochloride (Morphine-HCTL)

Homocysteine thiolactone hydrochloride (0.12 g, $7.8\times10^{-4}$ mol), (0.62 g, $7.8\times10^{-4}$ mol) pyridine and (0.296 g, 7.8×10$^{-4}$ mol) 3-O-carboxymethyl morphine hydrochloride were dissolved in 5 ml dimethylformamide. Addition of 1 ml of a dimethylformamide solution containing dicyclohexylcarbodiimide (0.177 g, 8.6×10$^{-4}$ mol) followed. The flask was purged with argon and the solution was stirred at 25° C. for 3 hr. The solvent was removed in vacuo and 20 ml water was added to the residue. The solution was stirred for 5 min, then the insoluble dicyclohexyl urea was filtered. The filtrate was washed with 10 ml methylene chloride. The pH of the aqueous layer was adjusted to 7 with an aqueous solution of saturated potassium carbonate. The aqueous solution was extracted 6 times with 10 ml methylene chloride. The combined organic extracts were dried with 2 g magnesium sulfate, filtered and the solvent removed in vacuo. Ethanol (20 ml) was added to the residue and evaporated in vacuo to remove the pyridine. Ethyl acetate (10 ml) was added and insoluble precipitates were filtered. Ethereal hydrochloric acid (1M) was added to the solution while stirring until the pH was red to litmus. The white solid was filtered and washed with ethyl acetate. The product was dried in vacuo and the yield was 316 mg.

Synthesis of p-Nitroamphetamine Hydrochloride d-Amphetamine sulfate (10 g, 2.7×10$^{-2}$ mol) was dissolved in sulfuric acid (5mL) and the solution was cooled in an ice-water bath. Fuming nitric acid (4.6 mL) was added dropwise to the reaction solution. The reaction mixture was stirred on the ice-water bath for 1 h after which it was poured over ice-water. Sodium hydroxide (10N) was added to adjust the solution to pH 12. The mixture was extracted with diethyl ether (2×100 mL), the combined organic layers were washed with water (2×100 mL) and were dried over anhydrous magnesium sulfate. The drying agent was removed by filtration and 1N ethereal hydrochloric acid was added to form the hydrochloride salt. The solvent was removed in vacuo. Acetone (200 mL) was added to the white residue and the suspension was stirred at room temperature for 2 h. The suspension was then filtered and the resulting white precipitate was recrystallized from ethanol/acetone to yield 3.5 g (60%) of p-nitroamphetamine hydrochloride as a white crystalline solid with a melting point of 191°–192° C.

Synthesis of p-Aminoamphetamine Dihydrochloride p-Nitroamphetamine hydrochloride (3.5 g, 1.6×10$^4$ mol) was dissolved in 200 ml methanol followed by the addition of 10% palladium-carbon (1.0 g) and ammonium formate (7.0 g). The reaction mixture was stirred at room temperature for 2 h. The catalyst was removed by filtration and the solvent was evaporated in vacuo. The partially crystalline residue was dissolved in 20 ml water and potassium hydroxide pellets were added to adjust the solution to pH 12. The solution was then extracted with methylene chloride (3×60 mL), the combined organic layers were washed with water (1×50 mL) and were dried over anhydrous magnesium sulfate. The drying agent was removed by filtration and 1N ethereal hydrochloric acid was added to form the hydrochloride salt. The solvent was removed in vacuo to give 2.0 g (56%) of p-aminoamphetamine dihydrochloride as a white crystalline solid with a melting point of 225°–240° C.

Synthesis of p-Acetylthiopropionamide Amphetamine Hydrochloride (Amphetamine-ATP)

p-Aminoamphetamine dihydrochloride (2.0 g, 9×10$^{-3}$ mol) was dissolved in anhydrous dimethylformamide (88 mol). Acetylthiopropionic acid (1.5 g, 1.0×10$^{-2}$ mol) was added followed by anhydrous pyridine (2.4 mL, 2.97×10$^{-2}$ mol) and 1-(3-dimethyl-aminopropyl)-3-ethylcarbodiimide hydrochloride (1.9 g, 1.0×10$^{-2}$ mol). The reaction mixture was stirred at room temperature for 1 h. The solvent was removed in vacuo. The residue was dissolved in water and washed with methylene chloride (3×50 mL), followed by the addition of 0.5M potassium phosphate, pH 7 (100 mL). The aqueous solution was washed again with methylene chloride (3×50 mL). The solvent was removed in vacuo. Ethanol (2×50 ml) was added and removed in vacuo to azeotrope off residual water. The dark yellow residue was triturated with methylene chloride (3×50 mL). Activated carbon (4.0 g) was added to the combined methylene chloride solution and was stirred at room temperature for 30 min. The carbon was removed by filtration and the solvent was evaporated in vacuo. The thick oil was redissolved in methylene chloride and acidified with 1N ethereal hydrochloric acid. The methylene chloride/diethyl ether solution was decanted off and the residue was dried in vacuo to give 1.2 g of the title compound as an orange crystalline solid.

Preparation of Ligand Analogues Attached to Keyhole Limpet Hemocyanin (KLH), Bovine Serum Albumin (BSA), and Alkaline Phosphatase (AP) for Antibody Screening Assays The attachment of the above ligand analogues, amphetamine-ATP and morphine-HCTL, to proteins is achieved by reacting the free thiol forms of the ligand analogues, generated by hydrolysis, to proteins which contain a reactive maleimide that is the result of derivatization of the protein with succinimidyl 4-(N-maleimidomethyl) cyclohexane-1-carboxylate (SMCC, Pierce Chemical Co.). The free thiol forms of the ligand analogues were generally reacted in substantial molar excess over the maleimide-protein to couple all of the reactive maleimides to the ligand analogue. The free thiol form of the amphetamine-ATP ligand analogue was generated by dissolving amphetamine-ATP in 0.12M potassium carbonate in 80% methanol/20% water. After 5 min at room temperature the thiol concentration was determined by reaction with DTNB by the method of Elman, (Arch. Biochem. Biophys., 82, 70 (1959)). The free thiol form of morphine-HCTL was generated by dissolving in 5.7 ml of 70% dimethylformamide/30% water and 1.43 ml 1N potassium hydroxide was added. After 5 min the thiol concentration was determined by reaction with DTNB. When the free thiol forms of the ligand analogues were added to maleimide-protein for coupling, the pH was adjusted to 7 if necessary.

KLH (6 ml of 14 mg/ml) was reacted with sulfosuccinimidyl 4-(N-maleimidomethyl)cyclohexane-1-carboxylate (SULFO-SMCC) by adding 15 mg of SULFO-SMCC and maintaining the pH between 7 and 7.5 with 1N potassium hydroxide over a period of one hour at room temperature while stirring. The protein was separated from the unreacted SULFO-SMCC by gel filtration chromatography in 0.1M potassium phosphate, 0.02M potassium borate, and 0.15M sodium chloride, pH 7.0, and 24 ml of KLH-maleimide was collected at a concentration of 3.1 mg/ml. The free thiol forms of the ligand analogues were added in excess over the KLH-maleimide to react with substantially all of the maleimides and the solution was stirred for 4 hours at 4° C. and then dialyzed against 3 volumes of one liter each of pyrogen-free phosphate-buffered saline, pH 7.4, prior to immunization of mice using standard techniques.

BSA (3.5 ml of 20 mg/ml) was reacted with SMCC by adding a solution of 6.7 mg of SMCC in 0.3 ml acetonitrile and stirring the solution for one hour at room temperature while maintaining the pH between 7 and 7.5 with 1N potassium hydroxide. The protein was separated from unreacted materials by gel filtration chromatography in 0.1M potassium phosphate, 0.02M potassium borate, 0.15M sodium chloride, pH 7.0. The free thiol forms of the ligand analogues were added in excess to the BSA-maleimide and the solution was stirred for 4 hours at 4° C. The solution was used to coat microtiter plates for the detection of antibodies that bind the ligand analogues by standard techniques.

AP (1.5 ml of 10.9 mg/ml) was reacted with SULFO-SMCC by adding 3.1 mg of SULFO-SMCC to the solution and stirring at room temperature for one hour while maintaining the pH between 7.0 and 7.5 using 1M potassium hydroxide. The protein was separated from the unreacted materials by gel filtration chromatography in 0.1M potassium phosphate, 0.02M potassium borate, 0.15M sodium chloride, pH 7.0. The free thiol form of the ligand analogues was added to the AP-maleimide (0.2 ml at 3.56 mg/ml) such that 10 moles of drug were added per mole of AP-maleimide, and the solutions were stirred for 1.5 hours at 4° C. The protein was separated from unreacted materials by gel filtration chromatography in 0.1M potassium phosphate, 0.02M potassium borate, 0.15M sodium chloride, pH 7.0, and the ligand analogue conjugates were diluted for use in assays.

Preparation Of Latex-Immobilized Affinity-Purified Goat IgG Antibody Against The Fc Fragment Of Mouse IgG Affinity-purified goat-anti-mouse Fc (BiosPacific) and polystyrene latex particles (sulfated, 1.07 gm) (Interfacial Dynamics) were incubated separately at 45° C. for one hour, the antibody solution being buffered with 0.1M 2-(N-morpholino) ethane sulfonic acid at pH 5.5. While vortexing the antibody solution, the suspension of latex particles was added to the antibody solution such that the final concentration of antibody was 0.3 mg/ml and the solution contained 1% latex solids. The suspension was incubated for 2 hours at 45° C. prior to centrifugation of the suspension to pellet the latex particles. The latex pellet was resuspended in 1% bovine serum albumin in phosphate-buffered-saline (PBS) and incubated for one hour at room temperature. Following centrifugation to pellet the latex, the pellet was washed three times by resuspension in PBS and centrifugation. The final pellet was resuspended in borate-buffered-saline, 0.1% sodium azide, pH 8.0, at a latex concentration of 1% solids. A 1% suspension of this latex preparation was capable of binding 40 $\mu$g/ml of monoclonal antibody.

Production and Primary Selection of Monoclonal Antibodies

Immunization of Balb/c mice was performed according to the method of Liu, D., Purssell, R., and Levy, J. G., *Clin Chem*, 25, 527–538 (1987). Fusions of spleen cells with SP2/0-Ag14 myeloma cells, propagation of hybridomas, and cloning were performed by standard techniques. Selection of hybridomas for further cloning began with culture supernatant at the 96-well stage. A standard ELISA procedure was performed with either morphine or amphetamine ligand analogues attached to BSA which was adsorbed to the ELISA plate. Typically, a single fusion was plated out in twenty plates and approximately 10–20 wells per plate were positive by the ELISA assay. At this stage, a secondary selection could be performed if antibodies to the SMCC part of the linking arm were to be eliminated from further consideration. An ELISA assay using BSA derivatized with SMCC but not coupled to the ligand analogue identified which of the positive clones that bound the ligand analogue coupled to BSA were actually binding the SMCC-BSA. Depending on the particular objectives for the antibodies obtained, the antibodies specific for SMCC-BSA can be eliminated at this step.

Assay for the Further Selection of Antibodies Binding the Target Ligand

Antibodies that are identified by the ELISA assay are subjected to further screening using the following assay method. Reaction mixtures containing 25 $\mu$l of an antibody dilution, 25 $\mu$l of diluent or a target ligand standard or a cross-reacting species, and 25 $\mu$l of ligand analogue conjugated to alkaline phosphatase were incubated for 20 minutes at room temperature in V-bottom microtiter plates. A 25 $\mu$l volume of a 1% suspension of goat-antimouse IgG (Fc specific) adsorbed to latex was added to each reaction mixture and incubated another 10 minutes. The reaction mixtures were then subjected to centrifugation at 3000 rpm (1500 g) in a swinging bucket rotor. A 25 $\mu$l volume of the supernatant from each well was assayed for enzyme activity. By determining the enzyme activity in wells where high affinity antibody is in substantial excess over the amount needed to bind all of the immunoreactive conjugate, the enzyme activity that was associated with enzyme that did not contain bindable ligand analogue was determined. This non-immunoreactive fraction of the activity of the supernatant was subtracted from the measured activity to determine the activity associated with the immunoreactive fraction. Initially high affinity antibodies were selected in this assay by serially diluting the antibody in the range from approximately 100 nM to below one nM antibody concentration in the reaction mixture while using approximately one nM of ligand analogue conjugate. The free immunoreactive conjugate enzyme activity was determined by assaying the supernatant and the bound immunoreactive conjugate enzyme activity was determined by subtracting the free immunoreactive activity from the total immunoreactive conjugate enzyme activity. Under these conditions antibodies exhibiting a bound/free enzyme activity ratio of greater than 10 when the antibody is in excess over the conjugate are considered high affinity antibodies and are particularly preferred for the present invention. By determining the ratio of free/bound as a function of target ligand concentration in such assays standard curves were developed and antibody cross-reactivity with ligands other than the target ligand were determined. Antibodies with high affinity for the target ligand and with cross-reactivities that were within assay design goals were used in the present invention for the assay of multiple ligands in a sample.

Preparation of SMCC-Bovine Serum Albumin 10/1 (SMCC-BSA 10/1)

SMCC (17.5 mg, $5.2–10^{-5}$ mol) in 0.87 ml acetonitrile was added to 17.5 ml of bovine serum albumin, BSA, (350 mg, $5.2 \times 10^{-6}$ mol) in 0.1M potassium phosphate, 0.1M potassium borate, 0.15M sodium chloride, pH 7.5. The solution was stirred at room temperature for 1 hr and the pH was maintained at 7–7.5 by addition of 1N potassium hydroxide. The protein solution was applied to a 2.5 cm×25 cm column containing GH25 resin (Amicon Corp.) equilibrated in 0.1M potassium phosphate, 0.02M potassium borate, 0.15M sodium chloride, pH 7. Collect 30 ml of SMCC-BSA at 10.5 mg/ml. Analysis of the SMCC-BSA for maleimide groups, by reacting the protein with mercaptoethanol in slight excess over the estimated maleimide groups and measuring the unreacted mercaptoethanol by DTNB, showed that an average of 7 maleimide groups were attached to each BSA. The protein solution was frozen at −70° C.

Preparation of SMCC-Bovine Serum Albumin 15/1 (SMCC-BSA 15/1)

SMCC (49.2 mg, $1.5 \times 10^{-4}$ mol) in 2.46 ml acetonitrile was added in 2 portions at a 10 min interval to 30 ml of bovine serum albumin, BSA, (600 mg, $9 \times 10^6$ mol) in 0.1M potassium phosphate, 0.1M potassium borate, 0.15M sodium chloride, pH 7.5. The solution was stirred at room temperature for 1 hr. The protein solution was dialyzed with a PYROSART ultrafiltration module with a molecular weight cut-off of 20,000 (Sartorious, Gottingen) against 0.1M potassium phosphate, 0.02M potassium borate, 0.15M sodium chloride, pH 7. Collect 83 ml of SMCC-BSA at 6 mg/ml. Analysis of the SMCC-BSA for maleimide groups, by reacting the protein with mercaptoethanol in slight excess over the estimated maleimide groups and measuring the unreacted mercaptoethanol by DTNB, showed that an average of 9 maleimide groups were attached to each BSA. The protein solution was frozen at −70° C.

Preparation of SMCC-Bovine Serum Albumin 50/1 (SMCC-BSA 50/1)

SMCC (7.5 mg, $2.2 \times 10^{-5}$ mol) in 0.37 ml acetonitrile was added to 2 ml of bovine serum albumin, BSA, (30 mg, $4.5 \times 10^{-7}$ mol) in 0.1M potassium phosphate, 0.1M potassium borate, 0.15M sodium chloride, pH 8.0. The solution was stirred at room temperature for 1 hr. The protein solution was applied to a 1 cm×25 cm column containing GH25 resin (Amicon Corp.) equilibrated in 0.1M potassium phosphate, 0.02M potassium borate, 0.15M sodium chloride, pH 7. Collect 5.2 ml of SMCC-BSA at 5.23 mg/ml. Analysis of the SMCC-BSA for maleimide groups, by reacting the protein with mercaptoethanol in slight excess over the estimated maleimide groups and measuring the unreacted mercaptoethanol by DTNB, showed that an average of 30 maleimide groups were attached to each BSA. The protein solution was frozen at −70° C.

Preparation of HCTLAM-BSA Crosstalk Inhibitor

The thiol ester of N-acetylhomocysteine thiolactone (Aldrich Chemical Co., St. Louis, Mo.) (10 mg, $6.28 \times 10^{-5}$ mol) was hydrolyzed by dissolving the compound in 1.26 ml of 70% dimethylformamide/30% water and adding 0.032 ml 10N potassium hydroxide. The free thiol (7.0 $\mu$mol in 0.14 mL) was added to SMCC-BSA (50:1, 5.2 mg in 1 mL) and reacted for 4 hours at room temperature. The protein solution was applied to a 1 cm×12 cm column containing CELLUFINE GH25 resin (Amicon Corp.) equilibrated in 0.1M potassium phosphate, 0.02M potassium borate, 0.15M sodium chloride, pH 7, in order to separate the unreacted materials from the protein. The HCTLAM-BSA product was stored at 4° C.

Preparation of BSA-AMPHETAMINE

Amphetamine-ATP (0.095 g, $3 \times 10^{-4}$ mol, example 12) was dissolved in 50 ml of 0.12M potassium carbonate in 80% methanol/20% water. After 5 min at room temperature the thiol concentration was determined by reaction with DTNB to be 25 mM. The amphetamine thiol (7.6 ml, $1.9 \times 10^{-4}$ mol) was added with stirring to 20.3 ml (0.4 g, $5.9 \times 10^{6}$ mol) of SMCC-BSA, 10/1. The pH of the solution was adjusted to 7 with 1N hydrochloric acid. The container was purged with argon and the solution was stirred at room temperature for 2 hr. The conjugate solution was then dialyzed with a PYROSART module against 10 mM (2-(N-morpholino) ethane sulfonic acid, pH 5.77 and 110 ml of 3.57 mg/ml BSA-amphetamine was collected. The protein solution was frozen at −70° C.

Preparation of BSA-MORPHINE

Morphine-HCTL (0.068 g, $1.3 \times 10^{-4}$ mol, example 9) was dissolved in 5.7 ml of 70% dimethylformamide/30% water and 1.43 ml 1N potassium hydroxide was added. After 5 min the thiol concentration was determined by reaction with DTNB to be 16.9 mM. The morphine thiol _(6.4 ml, $1.1 \times 10^{-4}$ mol) was added with stirring to 26.7 ml SMCC-BSA, 15/1, (0.16 g, $2.4 \times 10^{-6}$ mol). The container was purged with argon and the solution was stirred at room temperature for 2 hr. The protein solution was then dialyzed using a PYROSART module against 10 mM (2-(N-morpholino) ethane sulfonic acid, pH 5.77, and 29.5 ml of 5.39 mg/ml BSA-morphine was collected. The protein solution was frozen at −70° C.

Preparation of Colloidal Gold Conjugate

Colloidal gold was first prepared by dissolving gold chloride trihydrate in deionized water (1.36 g in 0.7 liters) and filtering the solution through a $0.2\mu$ filter. The filtered solution was added to round-bottom flask equipped with a heating mantle and the solution was heated to 85° C. A solution of trisodium citrate (2.54 g in 6.35 mL of deionized water) was added while stirring and the solution was held at 85° C., for 12 minutes before diluting it with 0.7 liters of deionized water at room temperature. Just prior to the adsorption of proteins to colloidal gold, one volume of 0.2M (2-(N-morpholino) ethane sulfonic acid (MES), pH 5.77, was added to 19 volumes of colloidal gold and mixed.

Mixtures of BSA and ligand analogues coupled to BSA were adsorbed to colloidal gold to form conjugates by the following procedure. A mixture of BSA, BSA-amphetamine, and BSA-morphine was prepared in 10 mM MES, pH 5.77, at a protein concentration of 6 mg/mL with the BSA-amphetamine representing 10% and the BSA-morphine representing 20% of the total protein in the mixture. One volume of each protein mixture was mixed with 19 volumes of the colloidal gold solution in separate preparations. The preparations were allowed to stand for 30 minutes at room temperature. The conjugates were subjected to centrifugation at 40,000 g for 20 minutes at 22° C. to pellet the conjugate. The supernatant was removed and the pellet was washed twice with a volume of 50 mM potassium phosphate, 10 mM borate, pH 7.0, equal to the starting volume by resuspending it and subjecting it to centrifugation as described. After the final centrifugation, the soft part of the pellet was resuspended in approximately 0.5 ml of the buffer and stored at 4° C. The absorbance at 540 nm was 164 for the 10% amphetamine/20% morphine conjugate. The absorbance at 540 nm was used in characterizing the concentration of conjugate used in an assay.

Assay for Amphetamine and Morphine

An assay for the simultaneous detection of amphetamine and morphine was performed by combining the following reagents: 10 $\mu$l of 0.5M potassium phosphate, 0.1M potassium borate, 0.75M sodium chloride, 50 mg/ml BSA, pH 7 (hereafter referred to as "buffer"), 80 $\mu$l of a urine sample, 3 $\mu$l of the colloidal gold conjugate, 14 $\mu$l of HCTLAM-BSA at 1.85 mg/ml, and 1.6 $\mu$l of a mixture of two monoclonal antibodies, 1.1 $\mu$l of a monoclonal anti-morphine at 14.2 mg/ml and 0.5 $\mu$l of monoclonal anti-amphetamine at 11.7 mg/ml. Urine samples containing known concentrations of morphine and amphetamine were prepared by dissolving amphetamine and morphine in drug-free urine. The reaction mixtures were vortexed and each was applied to a nylon membrane onto which were bound monoclonal antibodies to amphetamine and morphine (hereafter referred to as amph Ab and morp Ab, respectively). The antibodies were bound to discrete zones of the nylon membrane by applying 2 $\mu$l of 2 mg/ml amph Ab and 2 $\mu$l of 20 mg/ml morp Ab, each in a pH 3.0 buffer. The affinities of the solid phase antibodies are greater for the ligand analogue of the ligand analogue conjugate than for the ligand as taught in U.S. patent application Ser. No. 583,046, filed on Sep. 14, 1990, referred to herein by reference. The membrane was placed in contact with a grooved surface to form a capillary network as described in U.S. patent application Ser. No. 500,299, filed on Mar. 12, 1990, incorporated by reference herein. The membrane was washed to remove unbound conjugate with a solution containing 50 mM potassium borate, 150 mM sodium chloride and 0.02% (v/v) Triton X-100, pH 8. The color density of the colloidal gold conjugate bound to the membrane at each discrete zone was measured with a Minolta CR241 reflectometer and the data is expressed in terms of delta E*, which is a measure of the minimum color difference that can be perceived by the human eye. In general, a delta E* value of 2.5 is not visible to the human eye. A more complete description of this unit can be found in Color in Business, Science and Industry by D.B. Judd and G. Wyszecki, John Wiley and Sons. The assay results are in Table I.

TABLE I

| [Morphine] ng/ml | [Amphetamine] ng/ml | Morphine Response delta E* | Amphetamine Response delta E* |
| --- | --- | --- | --- |
| 0 | 0 | 2.4 | 2.6 |
| 100 | 0 | 0.6 | 0.5 |
| 200 | 0 | 1.0 | 1.6 |
| 400 | 0 | 3.4 | 1.3 |
| 600 | 0 | 8.4 | 1.5 |
| 1000 | 0 | 30.1 | 4.3 |
| 1500 | 0 | 33.0 | 4.2 |
| 0 | 100 | 2.5 | 1.3 |
| 0 | 200 | 1.5 | 1.1 |
| 0 | 400 | 2.8 | 2.3 |
| 0 | 600 | 2.1 | 8.4 |
| 0 | 1000 | 1.6 | 8.8 |
| 0 | 1500 | 4.2 | 15.4 |

The results show that the assay of amphetamine and morphine can be performed using a conjugate constructed in accordance with the present invention. The assay of each of the target ligands is substantially unaffected by the presence of the uncomplementary binding domains, ligand receptor, and target ligand.

I claim:

1. A conjugate capable of simultaneously detecting the presence or amount of at least two target ligands in a sample, and which avoids interference between ligands in a heterogenous assay, said conjugate comprising:
   a signal development element;
   at least two assay components coupled to said signal development element, each of said assay components capable of binding a complementary binding partner, wherein each of said assay components is either:
   (a) similar in size or larger than its complementary binding partner,
   (b) smaller than its complementary binding partner and coupled to a molecular structure that is similar in size or larger than the assay component's complementary binding partner, or
   (c) smaller than its complementary binding partner and the assay component is aggregated to create an aggregate, such that the aggregate is similar in size or larger than the assay component's complementary binding partner; and,
   whereby in a heterogenous assay, said conjugate simultaneously detects the presence of each of said at least two target ligands in said sample.

2. The conjugate of claim 1, wherein said signal development element is a polymer comprising one or more dyes.

3. The conjugate of claim 1, wherein said signal development element is a liposome comprising one or more dyes.

4. The conjugate of claim 1, wherein said signal development element is a latex particle comprising one or more dyes.

5. The conjugate of claim 1, wherein said signal development element is a metal sol.

6. The conjugate of claim 1, wherein said signal development element is colloidal gold.

7. The conjugate of claim 1, wherein said signal development element is an enzyme.

8. The conjugate of claim 1, wherein at least one assay component comprises a receptor for a target ligand.

9. The conjugate of claim 1, wherein at least one assay component comprises a ligand analogue of a target ligand.

10. Use of the conjugate of claim 1 to develop a signal in a heterogenous assay, whereby the presence or amount of at least two target ligands is simultaneously detected and interference between ligands is avoided.

11. A conjugate capable of detecting the presence or amount of at least two target ligands in a sample, and which avoids interference between ligands in a heterogenous assay, said conjugate comprising:
   a signal development element; and,
   at least two assay components coupled to said signal development element, a first assay component capable of binding a complementary binding partner which is a receptor for a first target ligand, and a second assay component capable of binding a complementary binding partner which is a receptor for a second target ligand, wherein each of said assay components is either:
   (a) similar in size or larger than its complementary binding partner,
   (b) smaller than its complementary binding partner and coupled to a molecular structure that is similar in size or larger than the assay component's complementary binding partner, or
   (c) smaller than its complementary binding partner and the assay component is aggregated to create an aggregate, such that the aggregate is similar in size or larger than the assay component's complementary binding partner; and,
   whereby in a heterogenous assay said first assay component is capable of binding said receptor for said first target ligand in the presence of said receptor for said second target ligand, and said second assay component is capable of binding said receptor for said second target ligand in the presence of said receptor for said first target ligand.

12. A conjugate capable of simultaneously detecting the presence or amount of at least two target ligands in a sample, and which avoids interference between ligands in a heterogenous assay, said conjugate comprising:
   a signal development element; and,
   at least two assay components coupled to said signal development element, at least one of said assay components capable of binding a complementary binding partner which is a ligand analogue of one of said target ligands, and another assay component is capable of binding a complementary binding partner which is a ligand analogue of another target ligand, wherein each of said assay components is either:
   (a) similar in size or larger than its complementary binding partner,
   (b) smaller than its complementary binding partner and coupled to a molecular structure that is similar in size or larger than the assay component's complementary binding partner, or
   (c) smaller than its complementary binding partner and the assay component is aggregated to create an aggregate, such that the aggregate is similar in size or larger than the assay component's complementary binding partner; and,
   whereby each ligand analogue can bind to each assay component when both said ligand analogues are present, and whereby in a heterogenous assay said conjugate simultaneously detects the presence or amount of each of said at least two target ligands.

13. A conjugate capable of simultaneously detecting the presence or amount of at least two target ligands in a sample, and which avoids interference between ligands in a heterogenous assay, said conjugate comprising:
   a signal development element; and,
   at least two assay components coupled to said signal development element, one of said assay components capable of binding a complementary binding partner which is one of said target ligands, and another assay component capable of binding a complementary binding partner which is another of said target ligands, wherein each of said assay components is either:
     (a) similar in size or larger than its complementary binding partner,
     (b) smaller than its complementary binding partner and coupled to a molecular structure that is similar in size or larger than the assay component's complementary binding partner, or
     (c) smaller than its complementary binding partner and the assay component is aggregated to create an aggregate, such that the aggregate is similar in size or larger than the assay component's complementary binding partner; and,
   whereby each assay component is capable of binding one of said target ligands in the presence of the other target ligands, and whereby in a heterogenous assay said conjugate simultaneously detects the presence of each of said at least two target ligands when said at least two target ligands are present in said sample.

14. A conjugate capable of simultaneously detecting the presence or amount of at least two target ligands in a sample, and which avoids interference between ligands in a heterogenous assay, said conjugate comprising:
   a signal development element;
   at least two assay components coupled to said signal development element, one of said assay components comprising a ligand receptor which binds to a complementary binding partner which is one of said target ligands, another of said assay components comprising a ligand receptor which binds to a complementary binding partner which is another target ligand, wherein each of said assay components is either:
     (a) similar in size or larger than its complementary binding partner,
     (b) smaller than its complementary binding partner and coupled to a molecular structure that is similar in size or larger than the assay component's complementary binding partner, or
     (c) smaller than its complementary binding partner and the assay component is aggregated to create an aggregate, such that the aggregate is similar in size or larger than the assay component's complementary binding partner; and,
   whereby in a heterogenous assay, said conjugate simultaneously detects the presence of each of said at least two target ligands when said at least two target ligands are present.

15. A conjugate capable of simultaneously detecting the presence or amount of at least two target ligands in a sample, and which avoids interference between ligands in a heterogenous assay, said conjugate comprising:
   a signal development element;
   at least two assay components coupled to said signal development element, a first assay component capable of binding a complementary binding partner which is a receptor for one of said target ligands, a second assay component capable of binding a complementary binding partner which is an analogue of another of said target ligands, wherein each of said assay components is either:
     (a) similar in size or larger than its complementary binding partner,
     (b) smaller than its complementary binding partner and coupled to a molecular structure that is similar in size or larger than the assay component's complementary binding partner, or
     (c) smaller than its complementary binding partner and the assay component is aggregated to create an aggregate, such that the aggregate is similar in size or larger than the assay component's complementary binding partner; and,
   whereby in a heterogenous assay said first assay component is capable of binding said target ligand receptor and said second assay component is capable of binding said ligand analogue of another target ligand when both said target ligand receptor and said ligand analogue of another target ligand are present.

16. A conjugate capable of detecting the presence or amount of at least two target ligands in a sample, and which avoids interference between ligands in a heterogenous assay, said conjugate comprising:
   a signal development element;
   at least two assay components coupled to said signal development element, a first assay component capable of binding a complementary binding partner which is a receptor for a target ligand and a second assay component capable of binding a complementary binding partner which is another target ligand, wherein each of said assay components is either:
     (a) similar in size or larger than its complementary binding partner,
     (b) smaller than its complementary binding partner and coupled to a molecular structure that is similar in size or larger than the assay component's complementary binding partner, or
     (c) smaller than its complementary binding partner and the assay component is aggregated to create an aggregate, such that the aggregate is similar in size or larger than the assay component's complementary binding partner; and,
   whereby said first assay component is capable of binding said receptor for one of said target ligands and said second assay component is capable of binding said another target ligand when both said receptor for said target ligand and said another target ligand are present in said sample.

17. A conjugate capable of detecting the presence or amount of at least two target ligands in a sample, and which avoids interference between ligands in a heterogenous assay, said conjugate comprising:
   a signal development element;
   at least two assay components coupled to said signal development element, a first assay component capable of binding a complementary binding partner which is a ligand analogue of a target ligand and a second assay component capable of binding a complementary binding partner which is another target ligand, wherein each of said assay components is either:
     (a) similar in size or larger than its complementary binding partner, (b) smaller than its complementary binding partner and coupled to a molecular structure that is similar in size or larger than the assay component's complementary binding partner, or (c) smaller than its complementary binding partner and the assay component is aggregated to create an aggregate, such that the aggregate is similar in size or larger than the assay component's complementary binding partner; and, whereby said first assay component is capable of binding said ligand analogue of a target ligand and said second assay component is capable of binding said another target ligand when both said ligand analogue and said another target ligand are present in said sample.

18. A conjugate capable of detecting the presence or amount of a target ligand, and which avoids interference between ligands in a heterogenous assay, said conjugate comprising:

a signal development element;

at least two assay components coupled to said signal development element, a first assay component capable of binding a complementary binding partner which is a ligand other than said target ligand and a second assay component capable of binding a complementary binding partner which is a receptor for said target ligand, wherein each of said assay components is either:

(a) similar in size or larger than its complementary binding partner, (b) smaller than its complementary binding partner and coupled to a molecular structure that is similar in size or larger than the assay component's complementary binding partner, or (c) smaller than its complementary binding partner and the assay component is aggregated to create an aggregate, such that the aggregate is similar in size or larger than the assay component's complementary binding partner; and, whereby in a heterogenous assay said first assay component is capable of binding a ligand other than said target ligand in the presence of said receptor for said target ligand, and said second assay component is capable of binding said receptor for said target ligand in the presence of said ligand other than said target ligand.

19. A conjugate capable of detecting the presence or amount of a target ligand, and which avoids interference between ligands in a heterogenous assay, said conjugate comprising:

a signal development element;

at least two assay components coupled to said signal development element, a first assay component capable of binding a complementary binding partner which is a ligand analogue of said target ligand and a second assay component capable of binding a complementary binding partner which is a different ligand, wherein each of said assay components is either:

(a) similar in size or larger than its complementary binding partner, (b) smaller than its complementary binding partner and coupled to a molecular structure that is similar in size or larger than the assay component's complementary binding partner, or (c) smaller than its complementary binding partner and the assay component is aggregated to create an aggregate, such that the aggregate is similar in size or larger than the assay component's complementary binding partner; and, whereby in a heterogenous assay said first assay component is capable of binding said ligand analogue in the presence of said another ligand, and said second assay component is capable of binding said different ligand in the presence of said ligand analogue.

20. A conjugate capable of detecting the presence or amount of a target ligand in a sample, and which avoids interference between ligands in a heterogenous assay, said conjugate comprising:

a signal development element;

at least two assay components coupled to said signal development element, a first assay component capable of binding a complementary binding partner which is a ligand other than said target ligand and a second assay component capable of binding a complementary binding partner which is said target ligand, wherein each of said assay components is either:

(a) similar in size or larger than its complementary binding partner, (b) smaller than its complementary binding partner and coupled to a molecular structure that is similar in size or larger than the assay component's complementary binding partner, or (c) smaller than its complementary binding partner and the assay component is aggregated to create an aggregate, such that the aggregate is similar in size or larger than the assay component's complementary binding partner; and, whereby said first assay component is capable of binding said ligand other than said target ligand and said second assay component is capable of binding said target ligand when both said ligand other than said target ligand and said target ligand are present.

21. An assay for simultaneously detecting in a sample the presence or amount of at least two target ligands, each ligand capable of competing with a single conjugate comprising a signal development element and at least two assay components, said assay comprising:

providing a solid phase comprising a first ligand receptor immobilized in a first discrete zone and a second ligand receptor immobilized in a second discrete zone;

providing a conjugate comprising at least two assay components, a first assay component capable of binding a complementary binding partner which is said first ligand receptor immobilized in said first discrete zone on said solid phase, and a second assay component capable of binding a complementary binding partner which is said second ligand receptor immobilized in said second discrete zone on said solid phase, wherein each of said assay components is either:

(a) similar in size or larger than its complementary binding partner, (b) smaller than its complementary binding partner and coupled to a molecular structure that is similar in size or larger than the assay component's complementary binding partner, or (c) smaller than its complementary binding partner and the assay component is aggregated to create an aggregate, such that the aggregate is similar in size or larger than the assay component's complementary binding partner;

contacting said conjugate, said sample and said solid phase; and, relating an amount of said conjugate bound to said first discrete zone to the presence or amount of said first target ligand and relating an amount of said conjugate bound to said second discrete zone to the presence or amount of said second target ligand in said sample.

22. An assay for simultaneously detecting in a sample the presence or amount of at least two target ligands, each ligand capable of competing with a single conjugate comprising a signal development element and at least two assay components, said assay comprising:

providing a conjugate comprising at least two assay components, a first assay component capable of binding a complementary binding partner which is a first ligand receptor, and a second assay component capable of binding a complementary binding partner which is a second ligand receptor, wherein each of said assay components is either:
  (a) similar in size or larger than its complementary binding partner,
  (b) smaller than its complementary binding partner and coupled to a molecular structure that is similar in size or larger than the assay component's complementary binding partner, or
  (c) smaller than its complementary binding partner and the assay component is aggregated to create an aggregate, such that the aggregate is similar in size or larger than the assay component's complementary binding partner;

providing said first ligand receptor and second ligand receptor, where said first ligand receptor is capable of binding to a first target ligand and said second ligand receptor is capable of binding a second target ligand;

providing a solid phase comprising in a discrete zone a ligand receptor capable of binding said first assay component, and in another discrete zone a ligand receptor capable of binding said second assay component;

contacting said sample, said conjugate and said first and second ligand receptors to form a reaction mixture;

contacting said reaction mixture with said solid phase; and, relating an amount of said conjugate bound to said first discrete zone to the presence or amount of said first target ligand and relating an amount of said conjugate bound to said second discrete zone to the presence or amount of said second target ligand in said sample.

23. An assay for simultaneously detecting the presence or amount of at least two target ligands in a sample, each ligand capable of competing with an analogue of that ligand for binding to a single conjugate comprising a signal development element and at least two assay components, said assay comprising:

providing a solid phase comprising a ligand analogue of a first ligand immobilized in a first discrete zone and a ligand analogue of a second ligand immobilized in a second discrete zone;

providing a conjugate comprising at least two assay components, a first assay component capable of binding a complementary binding partner which is said ligand analogue of said first ligand and a second assay component capable of binding a complementary binding partner which is said ligand analogue of said second ligand, wherein each of said assay components is either:
  (a) similar in size or larger than its complementary binding partner,
  (b) smaller than its complementary binding partner and coupled to a molecular structure that is similar in size or larger than the assay component's complementary binding partner, or
  (c) smaller than its complementary binding partner and the assay component is aggregated to create an aggregate, such that the aggregate is similar in size or larger than the assay component's complementary binding partner;

contacting said conjugate, said sample and said solid phase; and, relating an amount of said conjugate bound to said first discrete zone to the presence or amount of said first target ligand and relating an amount of said conjugate bound to said second discrete zone to the presence or amount of said second target ligand in said sample.

24. An assay for simultaneously detecting the presence or amount of at least two target ligands in a sample, each ligand capable of competing an analogue of that ligand for binding to a single conjugate comprising a signal development element and at least two assay components, said assay comprising:

providing a first ligand analogue construct for a first target ligand and second ligand analogue construct for a second target ligand;

providing a conjugate comprising at least two assay components, a first assay component capable of binding a complementary binding partner which is said first ligand analogue construct for said first target ligand and a second assay component capable of binding a complementary binding partner which is said second ligand analogue construct for said second target ligand, wherein each of said assay components is either:
  (a) similar in size or larger than its complementary binding partner,
  (b) smaller than its complementary binding partner and coupled to a molecular structure that is similar in size or larger than the assay component's complementary binding partner, or
  (c) smaller than its complementary binding partner and the assay component is aggregated to create an aggregate, such that the aggregate is similar in size or larger than the assay component's complementary binding partner;

providing a solid phase comprising a first ligand analogue immobilized in a first discrete zone and second ligand analogue immobilized in a second discrete zone, where said first ligand analogue is capable of binding said first assay component and said second ligand analogue is capable of binding said second assay component;

contacting said sample, said conjugate and said first and second ligand constructs to form a reaction mixture;

contacting said reaction mixture with said solid phase; and, relating an amount of said conjugate bound to said first discrete zone to the presence of amount of said first target ligand and relating an amount of said conjugate bound to said second discrete zone to the presence or amount of said second target ligand in said sample.

25. An assay for simultaneously detecting the presence or amount of at least two target ligands in a sample, the target ligands capable of binding to a single conjugate and binding to at least two different ligand receptors, where a first ligand receptor is immobilized in a first discrete zone on a solid phase and a second ligand receptor is immobilized in a second discrete zone on said solid phase, said assay comprising:

providing a conjugate comprising at least two assay components coupled to a signal development element, a first assay component capable of binding a complementary binding partner which is a first target ligand and a second assay component capable of binding a complementary binding partner which is a second target ligand, wherein each of said assay components is either:
(a) similar in size or larger than its complementary binding partner,
(b) smaller than its complementary binding partner and coupled to a molecular structure that is similar in size or larger than the assay component's complementary binding partner, or
(c) smaller than its complementary binding partner and the assay component is aggregated to create an aggregate, such that the aggregate is similar in size or larger than the assay component's complementary binding partner;

providing a solid phase comprising in a discrete zone a ligand receptor capable of binding said first ligand, and in another discrete zone a ligand receptor capable of binding said second target ligand;

contacting said conjugate and said solid phase with said sample; and, relating an amount of said conjugate bound to said first discrete zone to the presence or amount of said first target ligand, and relating an amount of said conjugate bound to said second discrete zone to the presence or amount of said second target ligand in said sample.

* * * * *